United States Patent
Pflueger et al.

(10) Patent No.: US 7,381,222 B2
(45) Date of Patent: Jun. 3, 2008

(54) STENT FOR MAINTAINING PATENCY OF A BODY REGION

(75) Inventors: D. Russell Pflueger, Monarch Beach, CA (US); Christopher Paul Thompson, Austin, TX (US)

(73) Assignee: Quiescence Medical, Inc., Irvine, CA (US)

( * ) Notice: Subject to any disclaimer, the term of this patent is extended or adjusted under 35 U.S.C. 154(b) by 558 days.

(21) Appl. No.: 10/748,761

(22) Filed: Dec. 30, 2003

(65) Prior Publication Data

US 2008/0065209 A1 Mar. 13, 2008

Related U.S. Application Data

(63) Continuation-in-part of application No. 10/624,915, filed on Jul. 22, 2003.

(60) Provisional application No. 60/436,945, filed on Dec. 30, 2002, provisional application No. 60/437,058, filed on Dec. 30, 2002.

(51) Int. Cl.
*A61M 11/00* (2006.01)

(52) U.S. Cl. .................. 623/15; 606/199; 128/848

(58) Field of Classification Search ............... 128/848, 128/858, 206.11, 206.12, 206.18, 206.27, 128/207.13, 207.18; 606/199, 204, 204.45; 623/1.14, 1.15, 1.18, 1.19, 1.2, 1.21, 1.22
See application file for complete search history.

(56) References Cited

U.S. PATENT DOCUMENTS

| | | | |
|---|---|---|---|
| 2,574,623 A | 11/1951 | Clyde | |
| 3,132,647 A | 5/1964 | Corniello | |
| 3,993,078 A | 11/1976 | Bergentz et al. | |
| 3,998,209 A | 12/1976 | Macvaugh | |
| 4,198,967 A | 4/1980 | Dror | |
| 4,304,227 A | 12/1981 | Samelson | |
| 4,572,186 A | 2/1986 | Gould et al. | |
| 4,580,568 A | 4/1986 | Gianturco | |
| 4,665,918 A | 5/1987 | Garza et al. | |
| 4,676,240 A | 6/1987 | Gardy | |
| 4,732,152 A | 3/1988 | Wallsten et al. | |
| 4,803,075 A | 2/1989 | Wallace et al. | |

(Continued)

FOREIGN PATENT DOCUMENTS

DE 19920114 5/1999

(Continued)

OTHER PUBLICATIONS

PCT International Search Report for PCT/US03/41560, Applicant: Quiescence Medical, Inc., Forms PCT/ISA/210 and PCT/ISA/220, dated Oct. 4, 2004, 4 pages.

(Continued)

*Primary Examiner*—Steven O. Douglas
(74) *Attorney, Agent, or Firm*—William A. English; Vista IP Law Group LLP

(57) ABSTRACT

An apparatus and method for maintaining patency of a vessel or other body region is provided. The apparatus includes an appliance having a non-circumferential form and being effective in maintaining patency or openness, or causing to become patent or open, a body region in which the appliance is located. The appliance may be formed of a flexible metallic struts structured to be submucosally implanted into a wall of the vessel or other body region.

24 Claims, 9 Drawing Sheets

U.S. PATENT DOCUMENTS

| | | | |
|---|---|---|---|
| 4,821,715 A | 4/1989 | Downing | |
| 4,830,008 A | 5/1989 | Meer | |
| 4,848,343 A | 7/1989 | Wallsten et al. | |
| 4,875,480 A | 10/1989 | Imbert | |
| 4,950,227 A | 8/1990 | Savin et al. | |
| 4,978,323 A | 12/1990 | Freedman | |
| 5,007,926 A * | 4/1991 | Derbyshire | 623/1.15 |
| 5,026,377 A | 6/1991 | Burton et al. | |
| 5,037,427 A | 8/1991 | Harada et al. | |
| 5,046,512 A | 9/1991 | Murchie | |
| 5,048,518 A | 9/1991 | Eliachar et al. | |
| 5,052,409 A | 10/1991 | Tepper | |
| 5,059,211 A * | 10/1991 | Stack et al. | 623/1.15 |
| 5,061,275 A | 10/1991 | Wallsten et al. | |
| 5,064,435 A | 11/1991 | Porter | |
| 5,071,407 A | 12/1991 | Termin et al. | |
| 5,078,720 A | 1/1992 | Burton et al. | |
| 5,117,816 A | 6/1992 | Shapiro | |
| 5,133,354 A | 7/1992 | Kallok | |
| 5,147,370 A | 9/1992 | McNamara et al. | |
| 5,176,618 A | 1/1993 | Freedman | |
| 5,178,156 A | 1/1993 | Takishima et al. | |
| 5,190,053 A | 3/1993 | Meer | |
| 5,201,757 A | 4/1993 | Heyn et al. | |
| 5,204,382 A | 4/1993 | Wallace et al. | |
| 5,258,028 A | 11/1993 | Ersek et al. | |
| 5,281,219 A | 1/1994 | Kallok | |
| 5,284,161 A | 2/1994 | Karell | |
| 5,292,331 A | 3/1994 | Boneau | |
| 5,306,294 A | 4/1994 | Winston et al. | |
| 5,355,874 A | 10/1994 | Bertram | |
| 5,360,401 A | 11/1994 | Turnland | |
| 5,372,600 A | 12/1994 | Beyar et al. | |
| 5,383,926 A * | 1/1995 | Lock et al. | 623/1.2 |
| 5,441,515 A * | 8/1995 | Khosravi et al. | 606/194 |
| 5,451,406 A | 9/1995 | Lawin et al. | |
| 5,456,662 A | 10/1995 | Edwards et al. | |
| 5,474,563 A | 12/1995 | Myler et al. | |
| 5,476,505 A | 12/1995 | Limon | |
| 5,494,029 A | 2/1996 | Lane et al. | |
| 5,514,131 A | 5/1996 | Edwards et al. | |
| 5,534,007 A | 7/1996 | St. Germain et al. | |
| 5,540,733 A | 7/1996 | Testerman et al. | |
| 5,571,135 A | 11/1996 | Fraser et al. | |
| 5,582,184 A | 12/1996 | Erickson et al. | |
| 5,591,216 A | 1/1997 | Testerman et al. | |
| 5,603,698 A | 2/1997 | Roberts et al. | |
| 5,611,355 A | 3/1997 | Hilsen | |
| 5,618,299 A * | 4/1997 | Khosravi et al. | 623/1.2 |
| 5,632,771 A | 5/1997 | Boatman et al. | |
| 5,642,737 A | 7/1997 | Parks | |
| 5,643,309 A | 7/1997 | Myler et al. | |
| 5,649,540 A | 7/1997 | Alvarez et al. | |
| 5,664,567 A | 9/1997 | Linder | |
| 5,669,377 A | 9/1997 | Fenn | |
| 5,674,191 A | 10/1997 | Edwards et al. | |
| 5,682,903 A | 11/1997 | Meade | |
| 5,683,451 A | 11/1997 | Lenker et al. | |
| 5,709,703 A | 1/1998 | Lukic et al. | |
| 5,718,224 A | 2/1998 | Muchin | |
| 5,718,702 A | 2/1998 | Edwards | |
| 5,738,114 A | 4/1998 | Edwards | |
| 5,772,668 A | 6/1998 | Summers et al. | |
| 5,776,142 A | 7/1998 | Gunderson | |
| 5,791,341 A | 8/1998 | Bullard | |
| 5,792,067 A | 8/1998 | Karell | |
| 5,792,478 A | 8/1998 | Lawin et al. | |
| 5,797,952 A | 8/1998 | Klein | |
| 5,800,379 A | 9/1998 | Edwards | |
| 5,815,904 A | 10/1998 | Clubb et al. | |
| 5,836,966 A | 11/1998 | St. Germain | |
| 5,843,021 A | 12/1998 | Edwards et al. | |
| 5,868,138 A | 2/1999 | Halstrom | |
| RE36,120 E | 3/1999 | Karell | |
| 5,893,365 A | 4/1999 | Anderson | |
| 5,897,579 A | 4/1999 | Sanders | |
| 5,911,752 A | 6/1999 | Dustrude | |
| 5,922,006 A | 7/1999 | Sugerman | |
| 5,950,624 A | 9/1999 | Hart | |
| 5,954,050 A | 9/1999 | Christopher | |
| 5,970,975 A | 10/1999 | Estes et al. | |
| 5,979,456 A | 11/1999 | Magovern | |
| 5,980,533 A | 11/1999 | Holman | |
| 5,983,136 A | 11/1999 | Kamen | |
| 5,988,170 A | 11/1999 | Thomas | |
| 6,004,342 A | 12/1999 | Filis | |
| 6,019,779 A | 2/2000 | Thorud et al. | |
| 6,022,343 A | 2/2000 | Johnson et al. | |
| 6,027,516 A | 2/2000 | Kolobow et al. | |
| 6,027,863 A | 2/2000 | Danadio, III | |
| 6,033,394 A | 3/2000 | Vidlund et al. | |
| 6,058,931 A | 5/2000 | Munchin | |
| 6,090,115 A | 7/2000 | Beyar et al. | |
| 6,092,523 A | 7/2000 | Belfer | |
| 6,098,616 A | 8/2000 | Lundy, Jr. et al. | |
| 6,106,541 A | 8/2000 | Hurbis | |
| 6,110,164 A | 8/2000 | Vidlund | |
| 6,123,082 A | 9/2000 | Berthon-Jones | |
| 6,126,611 A | 10/2000 | Bourgeois et al. | |
| 6,126,657 A | 10/2000 | Edwards et al. | |
| 6,129,084 A | 10/2000 | Bergersen | |
| 6,132,460 A | 10/2000 | Thompson | |
| 6,132,461 A | 10/2000 | Thompson | |
| 6,161,541 A | 12/2000 | Woodson | |
| 6,161,542 A | 12/2000 | Halstrom | |
| 6,171,314 B1 | 1/2001 | Rotramel | |
| 6,183,493 B1 | 2/2001 | Zammit | |
| 6,238,411 B1 | 5/2001 | Thorner | |
| 6,238,430 B1 | 5/2001 | Klumb et al. | |
| 6,240,316 B1 | 5/2001 | Richmond et al. | |
| 6,248,122 B1 | 6/2001 | Klumb et al. | |
| 6,250,307 B1 | 6/2001 | Conrad et al. | |
| 6,254,631 B1 | 7/2001 | Thompson | |
| 6,257,236 B1 | 7/2001 | Dutkiewicz | |
| 6,270,512 B1 | 8/2001 | Rittmann | |
| 6,273,876 B1 | 8/2001 | Klima et al. | |
| 6,305,376 B1 | 10/2001 | Thornton | |
| 6,312,463 B1 * | 11/2001 | Rourke et al. | 623/1.39 |
| 6,325,064 B1 | 12/2001 | Thornton | |
| 6,328,753 B1 | 12/2001 | Zammit | |
| 6,329,352 B1 | 12/2001 | Meyer et al. | |
| 6,345,202 B2 | 2/2002 | Richmond et al. | |
| 6,358,274 B1 | 3/2002 | Thompson et al. | |
| 6,363,935 B1 | 4/2002 | Boussignac | |
| 6,371,112 B1 | 4/2002 | Bibi | |
| 6,371,953 B1 | 4/2002 | Beyar et al. | |
| 6,371,979 B1 | 4/2002 | Beyar et al. | |
| 6,374,824 B1 | 4/2002 | Thornton | |
| 6,379,311 B1 | 4/2002 | Gaumond et al. | |
| 6,386,199 B1 | 5/2002 | Alfery | |
| 6,390,096 B1 | 5/2002 | Conrad et al. | |
| D458,679 S | 6/2002 | Thompson et al. | |
| 6,401,717 B1 | 6/2002 | Conrad et al. | |
| 6,406,490 B1 * | 6/2002 | Roth | 623/1.22 |
| 6,408,852 B2 | 6/2002 | Tielemans | |
| 6,415,796 B1 | 7/2002 | Conrad et al. | |
| 6,419,641 B1 | 7/2002 | Mark et al. | |
| 6,427,686 B2 | 8/2002 | Augustine et al. | |
| 6,431,174 B1 | 8/2002 | Knudson et al. | |
| 6,432,128 B1 * | 8/2002 | Wallace et al. | 623/1.11 |
| 6,439,238 B1 | 8/2002 | Brenzel et al. | |
| 6,447,522 B2 | 9/2002 | Gambale et al. | |
| 6,450,169 B1 | 9/2002 | Conrad et al. | |
| 6,453,905 B1 | 9/2002 | Conrad et al. | |

| | | |
|---|---|---|
| 6,474,339 B1 | 11/2002 | Grosbois et al. |
| 6,485,524 B2 | 11/2002 | Strecker |
| 6,488,700 B2 | 12/2002 | Klumb et al. |
| 6,502,574 B2 | 1/2003 | Walter et al. |
| 6,513,530 B2 | 2/2003 | Knudson et al. |
| 6,513,531 B2 | 2/2003 | Knudson et al. |
| 6,516,806 B2 | 2/2003 | Knudson et al. |
| 6,523,541 B2 | 2/2003 | Knudson et al. |
| 6,523,542 B2 | 2/2003 | Knudson et al. |
| 6,523,543 B2 | 2/2003 | Conrad et al. |
| 6,546,936 B2 | 4/2003 | Knudson et al. |
| 6,578,580 B2 | 6/2003 | Conrad et al. |
| 6,601,585 B1 | 8/2003 | Conrad et al. |
| 6,607,584 B2 | 8/2003 | Knudson et al. |
| 6,626,181 B2 | 9/2003 | Knudson et al. |
| 6,634,362 B2 | 10/2003 | Conrad et al. |
| 6,636,767 B1 | 10/2003 | Knudson et al. |
| 6,733,525 B2 * | 5/2004 | Pease et al. ............... 623/2.18 |
| 6,742,524 B2 | 6/2004 | Knudson et al. |
| 6,793,672 B2 * | 9/2004 | Khosravi et al. ......... 623/1.13 |
| 6,955,172 B2 | 10/2005 | Nelson et al. |
| 2001/0025642 A1 | 10/2001 | Conrad et al. |
| 2001/0044587 A1 | 11/2001 | Conrad et al. |
| 2001/0052344 A1 | 12/2001 | Doshi |
| 2003/0149488 A1 | 8/2003 | Metzger et al. |
| 2004/0010308 A1 * | 1/2004 | Zafrir-Pachter et al. ... 623/1.35 |
| 2004/0045555 A1 | 3/2004 | Nelson et al. |
| 2004/0045556 A1 | 3/2004 | Nelson et al. |
| 2004/0049102 A1 | 3/2004 | Nelson et al. |
| 2004/0139975 A1 | 7/2004 | Neslon et al. |
| 2004/0199045 A1 | 10/2004 | Knudson et al. |

FOREIGN PATENT DOCUMENTS

| | | |
|---|---|---|
| EP | 0292936 | 11/1988 |
| EP | 0706808 | 4/1996 |
| SU | 1553140 | 3/1990 |
| WO | 0059398 | 10/2000 |
| WO | 0119301 | 3/2001 |
| WO | 0123039 | 4/2001 |

OTHER PUBLICATIONS

Examiner Storer, European Patent Office, Office Action for related EP Patent Appl. No. 03800323.2-2310, May 14, 2007, 5 pages.

Examiner Patel/Attorney for Applicant, Office Actions and Applicant Responses for related U.S. Appl. No. 10/624,915 [QMI-3077], 101 pages.

Examiner Ali/Attorney for Applicant, Office Actions and Applicant Responses for related U.S. Appl. No. 11/126,649 [QMI-3077DIV], 59 pages.

* cited by examiner

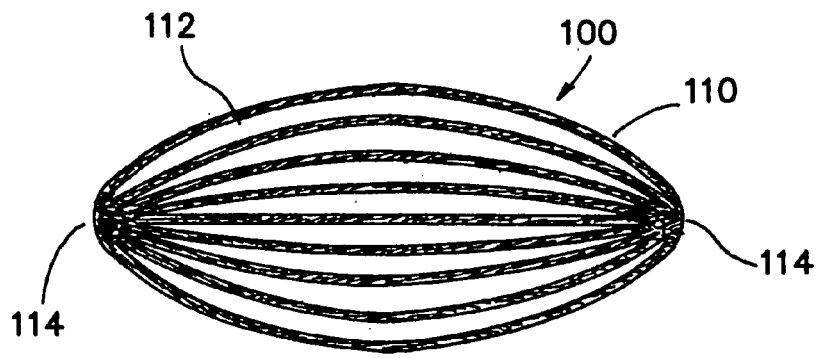
FIG. 6D
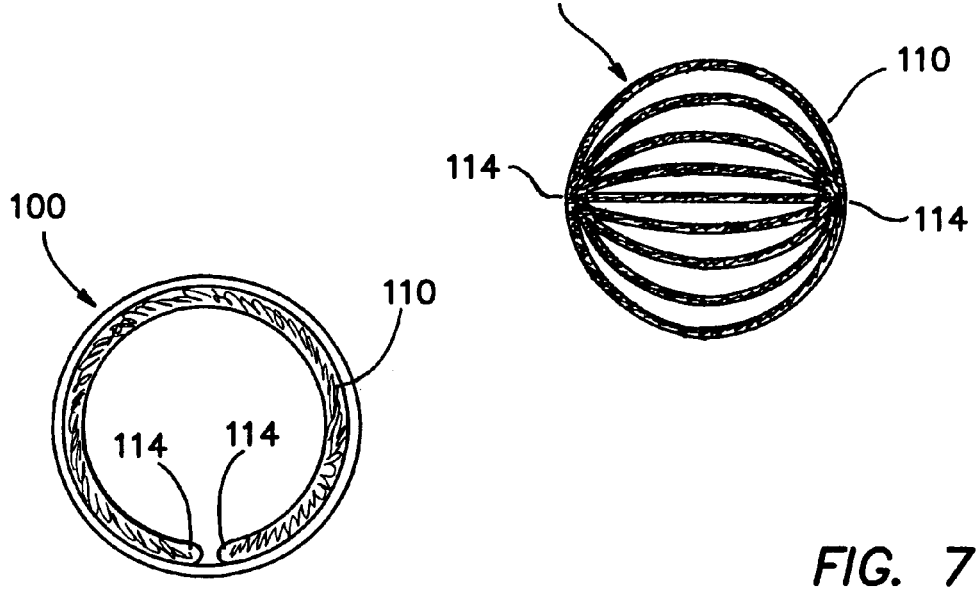
FIG. 6E
FIG. 6F
FIG. 7
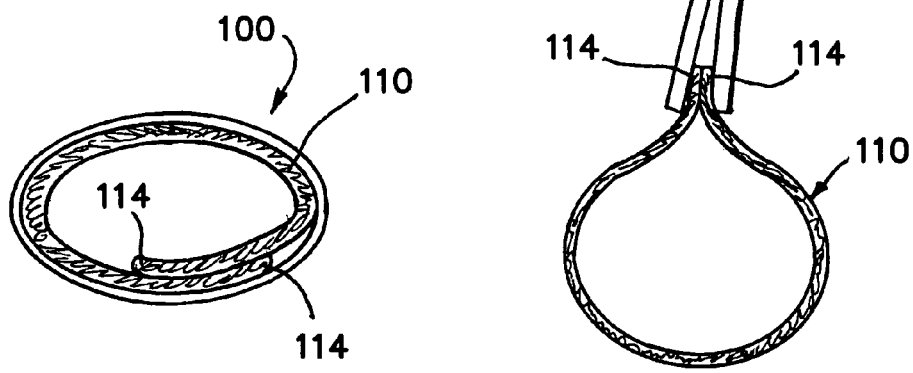
FIG. 6G

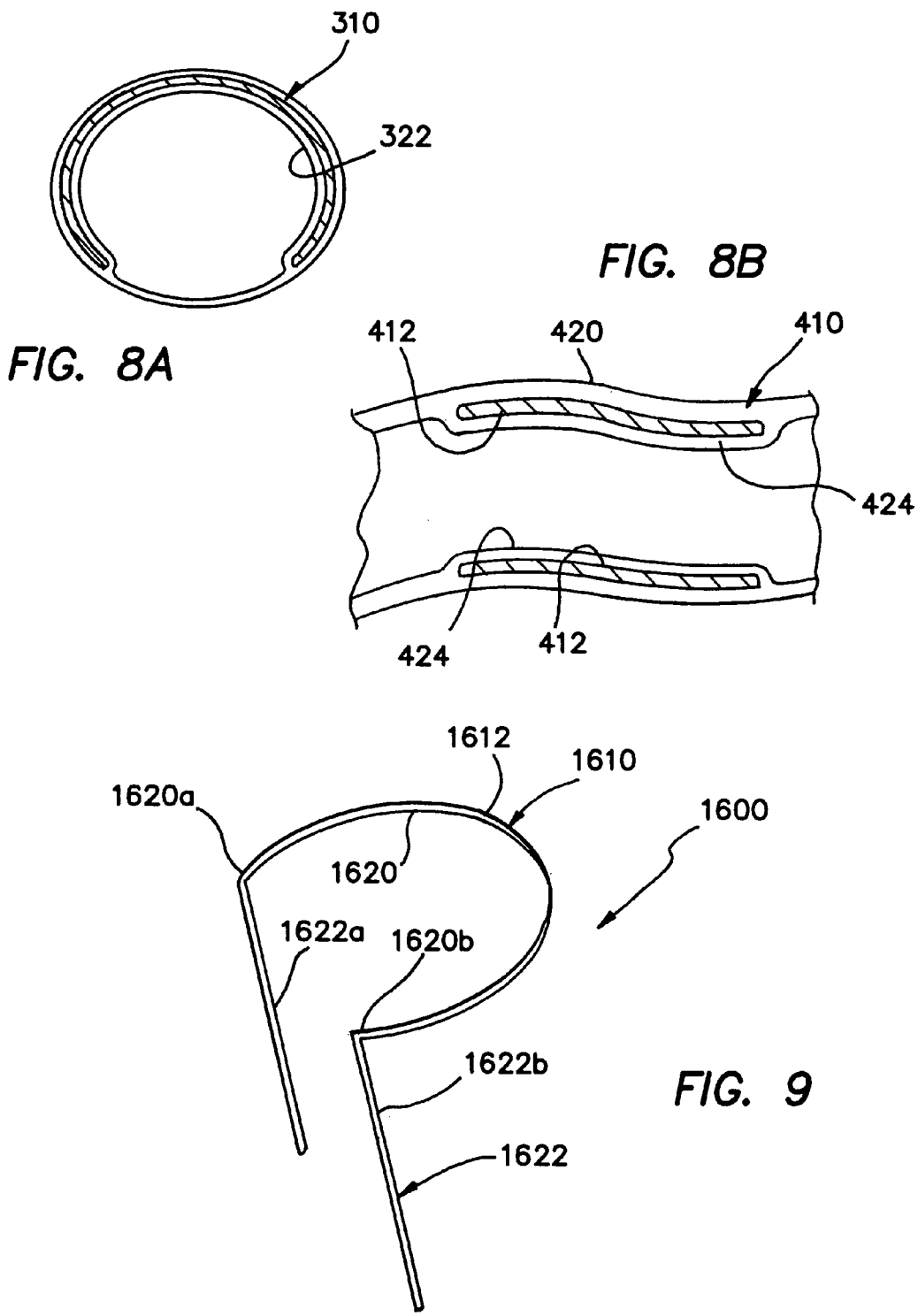

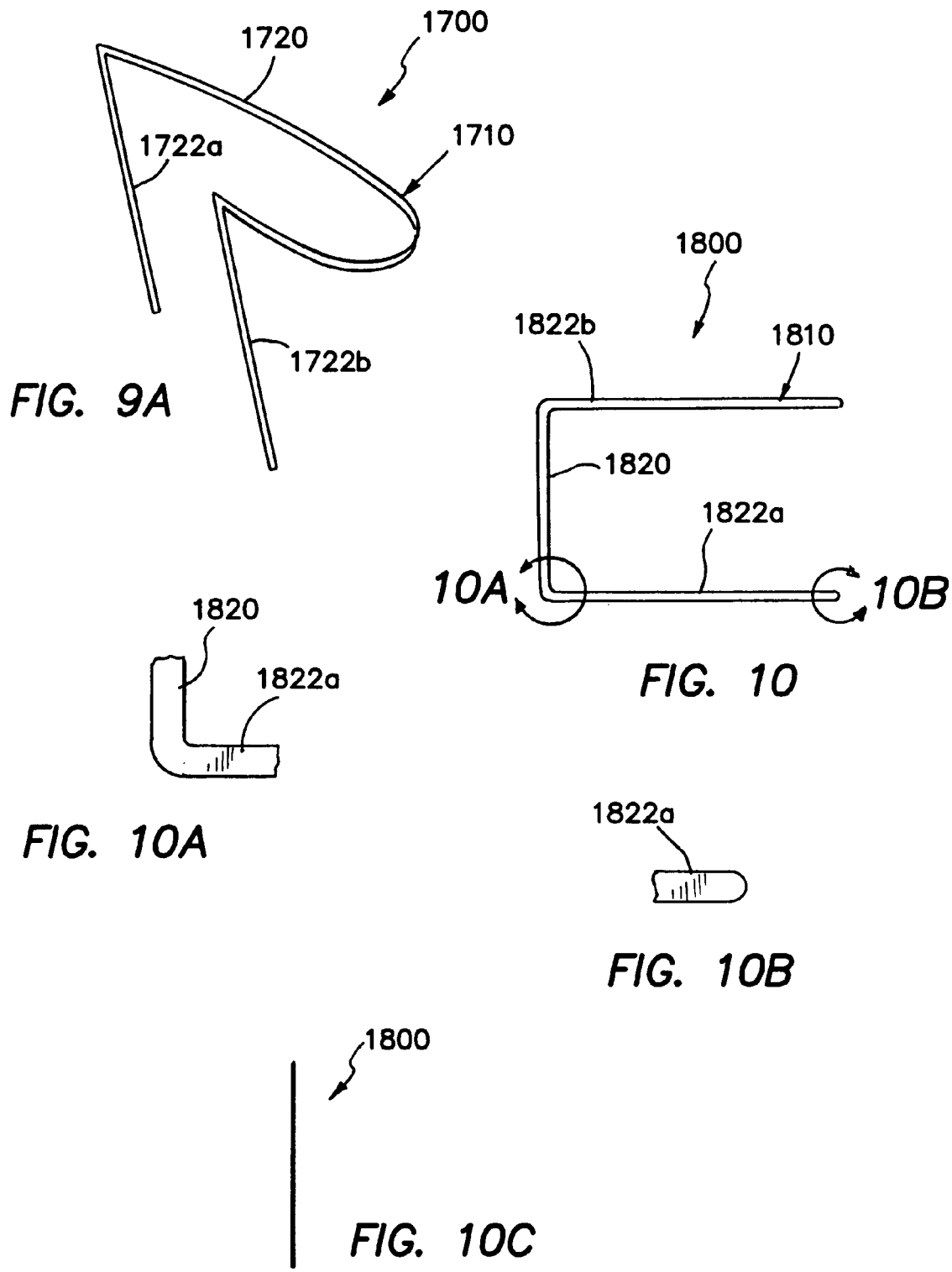

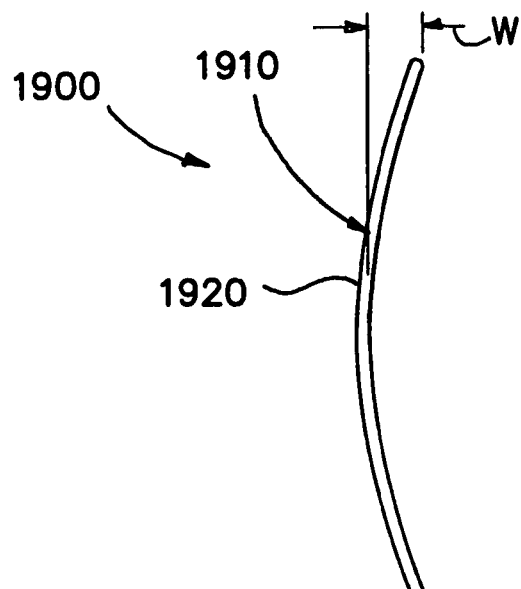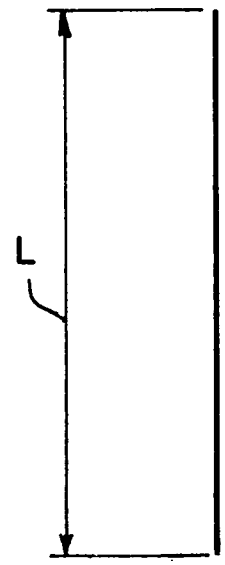
FIG. 11
FIG. 11A
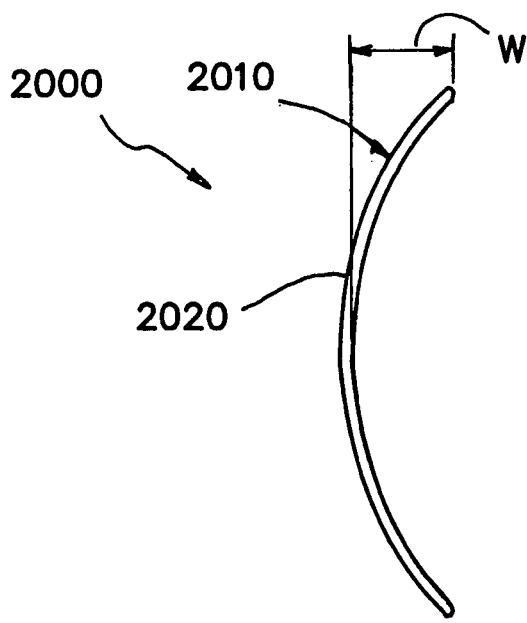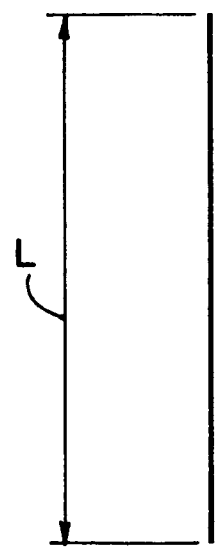
FIG. 12
FIG. 12A

STENT FOR MAINTAINING PATENCY OF A BODY REGION

RELATED APPLICATIONS

This application is a continuation-in-part of U.S. patent application Ser. No. 10/624,915, filed on Jul. 22, 2003, and claims the benefit of U.S. provisional application No. 60/436,945 filed on Dec. 30, 2002, and also claims the benefit of U.S. provisional application No. 60/437,058 filed on Dec. 30, 2002, the entire disclosures of which are incorporated herein by this specific reference.

BACKGROUND OF THE INVENTION

The present invention generally relates to medical devices and more specifically relates to a stent for maintaining patency of a body region.

There are many different kinds of endoprostheses, commonly called stents, which have the common characteristic of being presented into a patient's blood vessel or other body cavity or lumen in the shape of a cylinder, the wall of which forms a kind of lattice of deformable mesh in order to permit its diametrical expansion after being inserted into the body cavity in a contracted state.

A stent can maintain vascular patency by mechanically supporting vessels to prevent unintended closure. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens typically range in diameter from small coronary vessels of about 3 mm or less to about 28 mm or more in the aortic vessel.

A typical stent is a cylindrically shaped wire formed device intended to act as a permanent prosthesis. A stent is deployed in a body lumen from a radially compressed configuration into a radially expanded configuration which allows it to expand to provide support to a body lumen.

The stent can be made to be radially self-expanding or expandable by the use of an expansion device such as a balloon catheter. A self expanding stent is made from a resilient springy material while an expandable stent is made from a material which is permanently deformable. An expandable stent can be implanted during an angioplasty procedure by using a catheter bearing a stent which has been secured to the catheter such as in U.S. Pat. No. 5,372,600 to Beyar et al. which is incorporated herein by reference in its entirety.

Commonly, stents are made of stainless steel or highly elastic metal alloy wires which are interwoven into a cylindrical mesh. The open weave wire structure typically results in loose wires at ends of the stent which can be traumatizing to the vessel walls in contact therewith. Sharp edges and loose wires oftentimes result in a fibrous change therein and the formation of an intraluminal scar which can be the nexus of another stenosis.

The present invention provides an improved apparatus for maintaining patency and/or causing patency or openness in a vessel or other body region of a living human or animal body.

SUMMARY OF THE INVENTION

Accordingly, the present invention provides an apparatus effective to maintain patency or openness of a region of a human or animal body.

In a broad aspect of the invention, the apparatus comprises an appliance, preferably a self-expanding appliance, having a suitable structure, preferably a generally non-circumferential form or structure, and being effective in maintaining patency or openness or causing to become patent or open, the body region in which the appliance is located.

In one broad aspect, the present invention provides apparatus comprising an appliance sized and structured to be permanently (that is, for long term usage or for a relatively long time, such as at least about 1 week or about 1 month, preferably at least about 6 months, more preferably at least about 1 year, even more preferably about 5 years or longer) or temporarily implanted or placed in a body region of a human or animal.

The present apparatus may comprise any material or materials suitable for placement in the body region, for example vessel, which are effective to stiffen, reinforce and/or strengthen the region in order to provide support against collapse.

In one embodiment of the invention, the apparatus generally comprise an appliance sized and structured to be placed in a given position in a vessel or other body region, other than to facilitate a surgical procedure, and to be effective, when placed in the given position, to maintain patency thereof.

The appliance of the present invention is advantageously structured to have an enhanced, relative to a different device, ability to provide support against collapse of the vessel or other body region as well as to allow proper closure of the vessel or other body region as appropriate to normal healthy functioning thereof.

In one embodiment of the invention, the appliance comprises a substantially flat or planar member, when located outside the body in a resting or at rest position, including spaced apart end portions and a body portion joining the end portions. In this embodiment of the invention, the apparatus preferably is designed such that when the apparatus is appropriately positioned in the given position, the appliance takes on a curved configuration with end portions bearing against and supporting against collapse, the walls of the vessel or other body region. The appliance may be structured to form a diameter effective to adequately expand to at least partially circumscribe the vessel or other body region.

Advantageously, the apparatus may be structured to facilitate removal thereof from the region. For example, the apparatus may be structured such that when the apparatus is in other than the deployed configuration, for example, when the apparatus is located outside the body of the human or animal in a resting position, the appliance comprises a member that has a flexibility and resiliency that allows the appliance to be folded, rolled or coiled to take on a relatively smaller radius for facilitating insertion thereof into the region. When released into the region, the appliance unfolds, unrolls or uncoils, and provides pressure against one or more portions of the region, providing support thereto and maintaining or achieving patency of the region.

The appliance is preferably sized and structured to allow substantially natural normal functioning of the region when the appliance is located in the given position in the region.

Preferably, the appliance, when located in the body region, has a resiliency and flexibility, for example, resiliency and/or flexibility in at least one direction or at least two different directions or at least three different directions, that enables the appliance to provide an appropriate amount of support and reinforcement to walls of the vessel or other region while enabling substantially normal functioning of the region.

In some embodiments of the invention, the apparatus comprises an appliance which is structured to include an intrinsic ability to maintain patency of a vessel or other body region while allowing substantially normal, natural functioning thereof.

For example, the appliance may be structured to cause a reduced fibrotic reaction when placed in the pharyngeal region relative to a similar appliance that is structured from materials that will cause a fibrotic response, for example relative to a similar appliance that is made of polyester.

In some embodiments of the invention, the appliance having said intrinsic ability to maintain patency is structured to have smooth, radiused edges and smooth surfaces, for example in order to inhibit a fibrotic reaction of tissues when the appliance is placed in the pharyngeal region.

In some embodiments of the invention, the appliance is structured to cause the substantially no fibrotic reaction when placed in the pharyngeal region.

The appliance preferably comprises an elastic material. More preferably, the appliance comprises a super-elastic material. A number of suitable elastic and super-elastic materials are well known and can be employed in the present apparatus. One particularly useful material is a nickel titanium alloy, known as Nitinol.

In another aspect of the invention, a method for maintaining patency of a vessel or other body region comprises the steps of securing one or more elements to the region and allowing the elements to provide an opening force against the walls of the region, such opening force being sufficient to reinforce the walls against collapse while allowing substantially normal healthy functioning of the region.

Preferably, the method comprises placing at least partially submucosally, within the vessel or other body region of a patient, an appliance that is effective, when so placed, to maintain patency of the region.

Preferably, the step of placing comprises placing the apparatus substantially entirely submucosally, in the body region.

The apparatus, in accordance with an especially advantageous embodiment of the invention, is sized to be placed, at least partially, circumscribing an interior hollow passage defined by the vessel or other body region.

In another embodiment of the invention, the element may comprise an element that provides a magnetic opening force against collapsing vessel walls or other tissues. For example, the element may comprise an appliance, such as described and shown elsewhere herein, that is at least partially magnetized. More specifically, the element may comprise two or more magnetic elements having like poles facing one another, to create a magnetic field that can be utilized to provide a useful opening force to the vessel or other body region being treated.

In yet another embodiment of the invention, a method is provided for maintaining patency of a vessel or other body region of a human or an animal for purposes other than surgery. The method generally comprises the steps of providing a member in a substantially flat or precurved configuration, the member having a body portion and end portions spaced apart by the body portions, and implanting the member, at least partially submucosally, within the body region.

The method may further comprise the step of pretreating the member, for example, heat treating the member to cause the member to take on a desired curved configuration prior to the introduction of the member into the body.

Advantageously, the member is effective to provide a substantially constant force against at least a portion of the wall or walls of the body region.

For example, the step of implanting may comprise implanting the member into region such that the member is substantially entirely submucosally implanted therein.

In yet another related embodiment of the invention, a method for maintaining patency of a vessel or other body region of a human or animal for purposes other than surgery is provided wherein, the method generally comprises the steps of causing a tissue reaction of a body region of the patient, said tissue reaction being effective in at least one of strengthening and stiffening walls of the region. For example, the step of causing a tissue reaction may comprise applying an active agent to the walls of the region or, for example, placing at least one member, submucosally, into the walls. The member may have an intrinsic ability to provide support to the wall. For example, the member may be structured so that it will provide strengthening to the walls of the body region without relying upon a fibrotic or other reaction of the body tissue.

Certain embodiments of the invention may be better understood with reference to PCT Application No. PCT/US2003/41560, filed on Dec. 30, 2003, entitled APPARATUS AND METHODS FOR TREATING SLEEP APNEA, having the entire disclosure of which is incorporated herein by this specific reference.

Incorporated herein by this specific reference is the entire disclosure of each of the following patents:

Fraser et al U.S. Pat. No. 5,571,135, Turnland U.S. Pat. No. 5,360,401, Winston et al U.S. Pat. No. 5,306,294, Heyn et al U.S. Pat. No. 5,201,757, Burton et al U.S. Pat. No. 5,078,720, Termin et al U.S. Pat. No. 5,071,407, Porter U.S. Pat. No. 5,064,435, Wallsten et al is U.S. Pat. No. 5,061,275, Burton et al U.S. Pat. No. 5,026,377, Savin et al U.S. Pat. No. 4,950,227, Imbert U.S. Pat. No. 4,875,480, Wallsten et al U.S. Pat. No. 4,848,343, Wallsten et al U.S. Pat. No. 4,732,152, Garza et al U.S. Pat. No. 4,665,918, Gould et al U.S. Pat. No. 4,572,186, Strecker U.S. Pat. No. 6,485,524 B2, Klumb et al U.S. Pat. No. 6,488,700 B2, Klumb et al U.S. Pat. No. 6,248,122 B1, Klumb et al U.S. Pat. No. 6,238,430 B1, Harada et al U.S. Pat. No. 5,037,427, McNamara et al U.S. Pat. No. 5,147,370, Kolobow et al U.S. Pat. No. 6,027,516, Thorud et al U.S. Pat. No. 6,019,779, Holman U.S. Pat. No. 5,980,533, St. Germain U.S. Pat. No. 5,836,966, Klein U.S. Pat. No. 5,797,952, Gunderson U.S. Pat. No. 5,776,142, Summers et al U.S. Pat. No. 5,772,668, Lukic et al U.S. Pat. No. 5,709,703, Lenker et al U.S. Pat. No. 5,683,451, Bergentz et al U.S. Pat. No. 3,993,078, Myler et al U.S. Pat. No. 5,474,563, Limon U.S. Pat. No. 5,476,505, St. Germain et al U.S. Pat. No. 5,534,007, Roberts et al U.S. Pat. No. 5,603,698, Boatman et al U.S. Pat. No. 5,632,771, Myler et al U.S. Pat. No. 5,643,309, Strecker U.S. Pat. No. 6,485,524 B2, Augustine et al U.S. Pat. No. 6,427,686 B2, Linder U.S. Pat. No. 5,664,567, Downing U.S. Pat. No. 4,821,715, Alfery U.S. Pat. No. 6,386,199 B1, Lane et al U.S. Pat. No. 5,494,029, Grosbois et al U.S. Pat. No. 6,474,339 B1, Bullard U.S. Pat. No. 5,791,341, Gianturco U.S. Pat. No. 4,580,568, Hart U.S. Pat. No. 5,950,624, Zammit U.S. Pat. No. 6,328,753 B1, Woodson U.S. Pat. No. 6,161,541, Mark et al U.S. Pat. No. 6,419,641 B1, Thompson et al U.S. Pat. No. D458,679 S, Beyar et al U.S. Pat. No. 6,371,979 B1, Beyar et al U.S. Pat. No. 6,371,953 B1, Thompson U.S. Pat. No. 6,358,274 B1, Klima et al U.S. Pat. No. 6,273,876 B1, Thompson U.S. Pat.

No. 6,254,631 B1, Thompson U.S. Pat. No. 6,132,461, Thompson U.S. Pat. No. 6,132,460, Vidlund U.S. Pat. No. 6,110,164, Beyar et al U.S. Pat. No. 6,090,115, Vidlund et al U.S. Pat. No. 6,033,394, Donadio, III U.S. Pat. No. 6,027,863, Johnson et al U.S. Pat. No. 6,022,343, Thorud et al U.S. Pat. No. 6,019,779, Dustrude et al U.S. Pat. No. 5,911,752, Clubb et al U.S. Pat. No. 5,815,904, Eliachar et al U.S. Pat. No. 5,048,518, Conrad et al U.S. Pat. No. 6,450,169, Bibi U.S. Pat. No. 6,371,112, Thornton U.S. Pat. No. 6,325,064, Thornton U.S. Pat. No. 6,305,376, Thornton U.S. Pat. No. 6,374,824, Dutkiewicz U.S. Pat. No. 6,257,236, Rittmann U.S. Pat. No. 6,270,512, Thorner U.S. Pat. No. 6,238,411, Hurbis U.S. Pat. No. 6,106,541, Lundy, Jr. et al U.S. Pat. No. 6,098,616, Muchin U.S. Pat. No. 6,058,931, Filis U.S. Pat. No. 6,004,342, Christopher U.S. Pat. No. 5,954,050, Boussignac U.S. Pat. No. 6,363,935, Muchin U.S. Pat. No. 5,718,224, Conrad et al U.S. Pat. No. 6,250,307, Conrad et al U.S. Pat. No. 6,401,717, Conrad et al U.S. Pat. No. 6,390,096, Berthon-Jones U.S. Pat. No. 6,123,082, Halstrom U.S. Pat. No. 6,161,542, Halstrom U.S. Pat. No. 5,868,138, Tielemans U.S. Pat. No. 6,408,852, Shapiro U.S. Pat. No. 5,117,816, Bergersen U.S. Pat. No. 6,129,084, Edwards et al U.S. Pat. No. 6,126,657, Edwards U.S. Pat. No. 5,800,379, Edwards U.S. Pat. No. 5,738,114, Rotramel U.S. Pat. No. 6,171,314, Anderson U.S. Pat. No. 5,893,365; Thomas U.S. Pat. No. 5,988,170, Gaumond et al U.S. Pat. No. 6,379,311, Belfer U.S. Pat. No. 6,092,523, Richmond et al U.S. Pat. No. 6,345,202, Meyer et al U.S. Pat. No. 6,329,352, Estes et al U.S. Pat. No. 5,970,975, Bourgeois et al U.S. Pat. No. 6,126,611, Samelson U.S. Pat. No. 4,304,227, Dror U.S. Pat. No. 4,198,967, Gardy U.S. Pat. No. 4,676,240, Meade U.S. Pat. No. 5,682,903, Alvarez et al U.S. Pat. No. 5,649,540, Parks U.S. Pat. No. 5,642,737, Hilsen U.S. Pat. No. 5,611,355, Zammit U.S. Pat. No. 6,183,493.

Each and every feature described herein, and each and every combination of two or more of such features, is included within the scope of the present invention provided that the features included in such a combination are not mutually inconsistent.

These and other aspects of the present invention are apparent in the following detailed description and claims, particularly when considered in conjunction with the accompanying drawings in which like parts bear like reference numerals.

BRIEF DESCRIPTION OF THE DRAWINGS

FIG. 2b shows a front view of the apparatus shown in FIG. 2a.

FIG. 2c shows a top view of the apparatus shown in FIG. 2a.

FIG. 2d shows an end portion of the apparatus shown in FIG. 2a.

FIG. 2e shows a perspective view of another embodiment of the apparatus of the present invention similar to the embodiment shown in FIG. 2a.

FIGS. 6a-6e show different views of the apparatus shown in FIG. 5.

FIGS. 6f and 6g show simplified cross-sectional views of an apparatus of the present invention as deployed in vessels of different sizes.

FIG. 7 shows a simplified diagram of an apparatus of the invention folded for facilitating insertion of the apparatus into a vessel.

FIG. 8a shows a simplified cross-sectional view of an apparatus of the present invention submucosally implanted into a vessel wall.

FIG. 8b shows a simplified side view of an apparatus of the invention comprising spaced apart elongated elements or struts that are implanted in a vessel in alignment with a longitudinal axis of the vessel.

FIG. 9 shows a simplified perspective view of another embodiment of the invention including an element having a transverse portion and two substantially longitudinal portions depending from, and spaced apart by, the transverse portion.

FIG. 9A shows a simplified perspective view of an embodiment of the invention similar to the embodiment shown in FIG. 9, in which the transverse portion is sloped downwardly with respect to the longitudinal portions.

FIG. 10 shows another embodiment of the invention similar to the embodiment shown in FIG. 9, wherein the apparatus includes an appliance having a substantially planar, substantially U-shaped configuration.

FIG. 10A shows a magnified view of a portion of the apparatus circumscribed by line A of FIG. 10.

FIG. 10B shows a magnified view of a portion of the apparatus circumscribed by line B of FIG. 10.

FIG. 10C shows a side view of the apparatus of FIG. 10.

FIG. 11 shows a plan view of another embodiment of the invention comprising a substantially bow shaped element.

FIG. 11A shows a side view of the embodiment of the invention shown in FIG. 11.

FIG. 12 shows a plan view of yet another embodiment of the invention similar to the embodiment shown in FIG. 11 but having a different radius of curvature.

FIG. 12A shows a side view of the embodiment of the invention shown in FIG. 12.

DETAILED DESCRIPTION OF THE INVENTION

Figure 1:
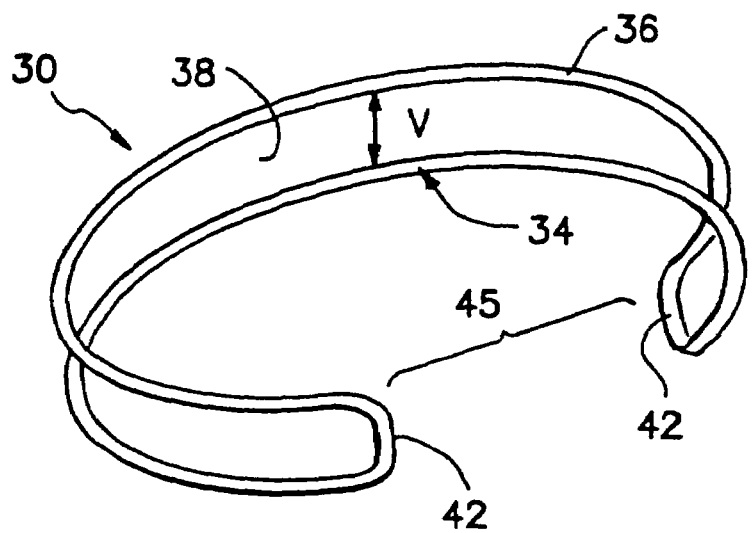
FIG. 1 shows a perspective view of an apparatus of the present invention.

Turning now to FIG. 1, an apparatus 30 in accordance with the invention is shown. The apparatus 30 comprises an appliance 34 in the form of a substantially C-shaped member having resilient, flexible wire struts 36. The struts 36 may have a circular, oval rounded or flattened transverse cross section. In this particular embodiment of the invention, the struts 36 form a continuous loop defining an open interior space 38. The appliance 34 includes end portions, preferably rounded end portions 42, that are spaced apart as shown.

The appliance 34 is structured to be positioned within the body region and against walls or tissue thereof to provide support thereof, for example, flexible, dynamic support. In a self expanding configuration, the apparatus may be flat in its native state or pre-curved to a diameter equal to or larger than the diameter of the target vessel in order to maintain constant pressure against an inner lumen of the target vessel. The end portions 42 may be spaced apart by a portion of the lumen or other tissues of the region. In some embodiments of the invention, the end portions touch or contact one another and/or overlap when the appliance is deployed in the body region. Spaced apart end portions 42 may define a gap 45 which in some embodiments of the invention is sized and/or structured to allow substantially normal functioning of a portion of the body region, or to provide minimal contact of the appliance 30 with an area, for example, a sensitive area, of the body region being maintained or caused to be maintained patent or open.

Figure 2A:
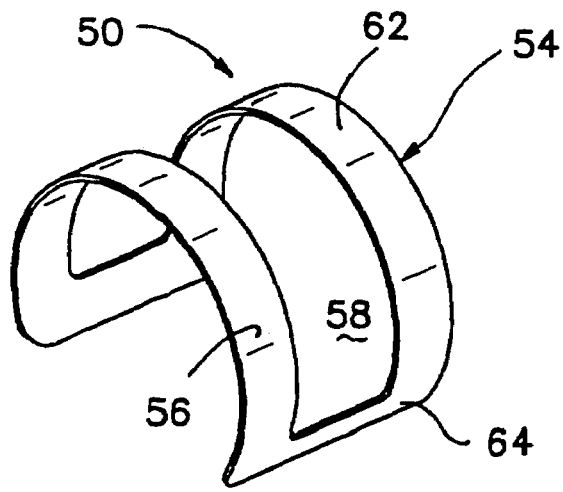
FIG. 2a shows a perspective view of another embodiment of an apparatus of the present invention.
Figure 2B:
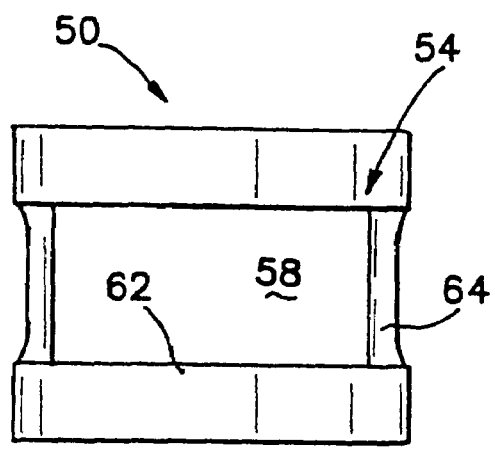
Figure 2C:
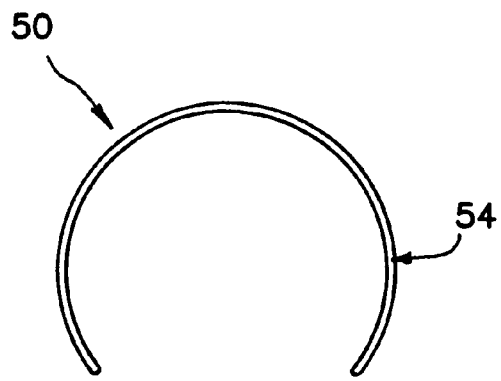

FIGS. 2a-2e show another embodiment of the apparatus of the invention similar to the embodiment shown in FIG. 1. A primary difference between the apparatus 50 shown in FIG. 2a and the apparatus 30 shown in FIG. 1 is that apparatus 50 comprises an appliance 54 comprising a relatively wider, outer peripheral portion 56, or flattened band, rather than struts 36 in order to contact a greater area of tissue for better tissue coverage, or greater hoop strength or opening pressure. The outer peripheral portion 56 defines an open interior space 58. FIG. 2b shows a front view of the appliance 54 and FIG. 2c shows a top view of the appliance 54 when placed in the body region. As shown in FIG. 2b, the open interior space 58 defined by the outer peripheral portion 56 remains open when placed in the body region. As shown, the peripheral portion 56 may have relatively wide side portions 62 and relatively narrow end portions 64.

Figure 2D:
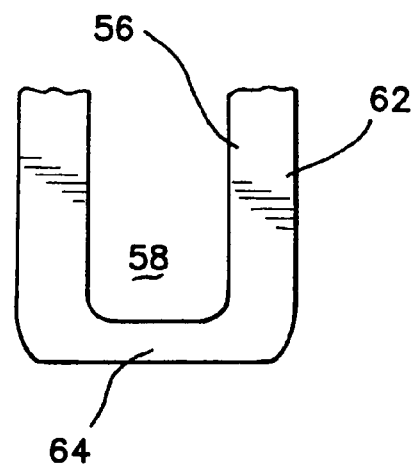

Referring to FIG. 2d, it can be appreciated that the appliance 54 may take the form of a flat configuration, for example, a flat rectangular configuration, having a substantially rectangular interior open space 58 prior to being curved into the cuff shape shown in FIGS. 2a-2c.

Figure 2E:
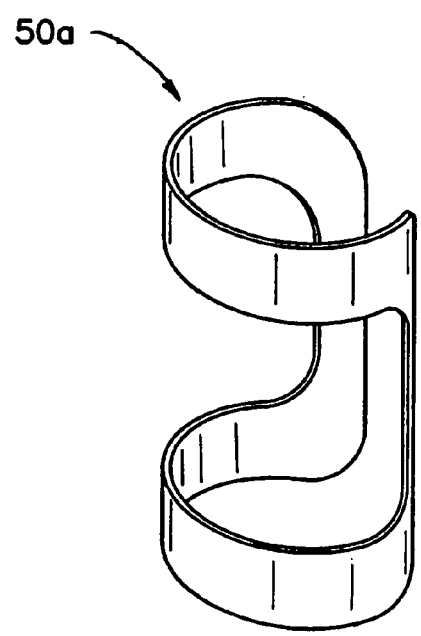

FIG. 2e shows a similar cuff-shaped embodiment 50a being configured for an elongated, relatively narrow vessel or body region.

It is to be appreciated that the dimensions provided herein and on the appended drawings are for purposes of example only. The dimensions of the apparatus may vary depending on the body region in which the apparatus is intended for use.

Figure 3A:
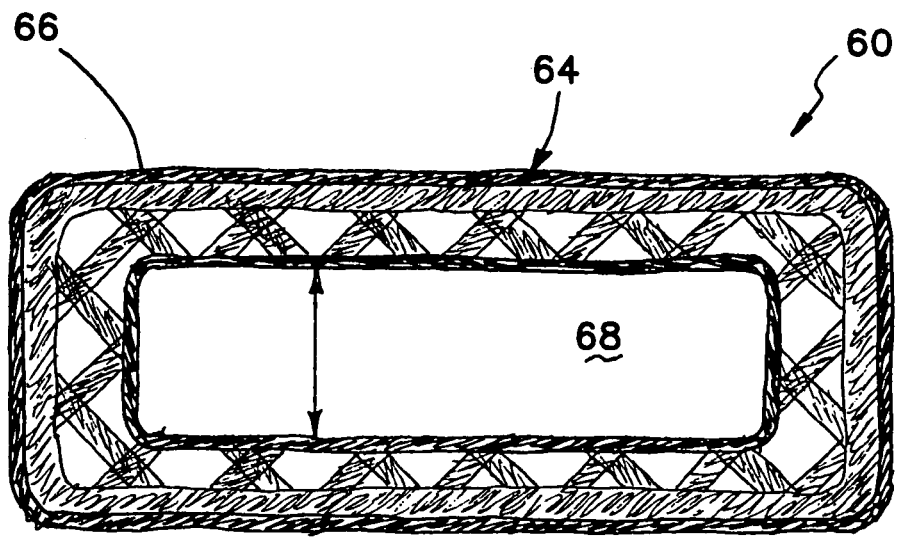
FIGS. 3a-3c show different views of another embodiment of an apparatus of the present invention.
Figure 3B:
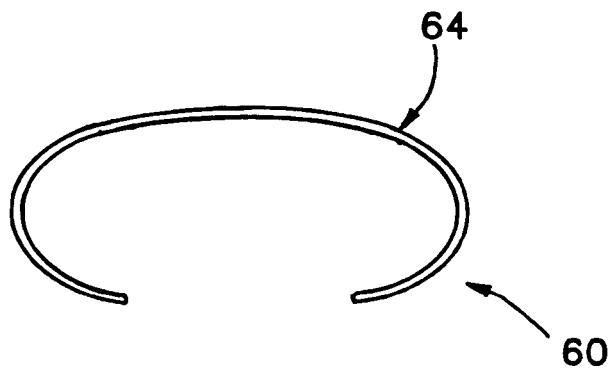
Figure 3C:
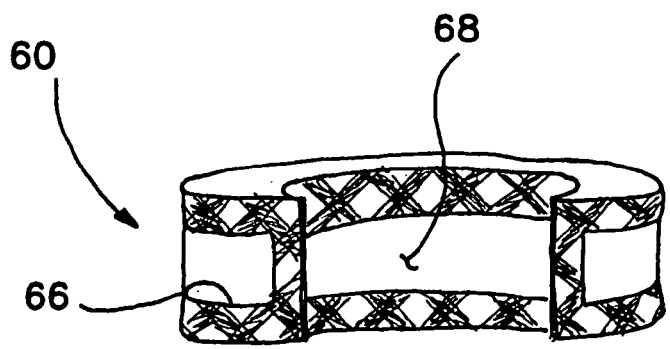

FIGS. 3a, 3b and 3c show another apparatus 60 in accordance with the invention similar to the embodiment shown in FIGS. 2a-2d and the embodiment shown in FIG. 2e. The primary difference between the apparatus 60 shown in FIGS. 3a-3c and FIGS. 2a-2e is that the apparatus 60 comprises a substantially mesh appliance 64, for providing increased flexibility and/or to facilitate tissue ingrowth. For example the appliance 64 comprises an outer peripheral portion 66 made of a woven mesh wire for example, defining an interior space 68.

Figure 4A:
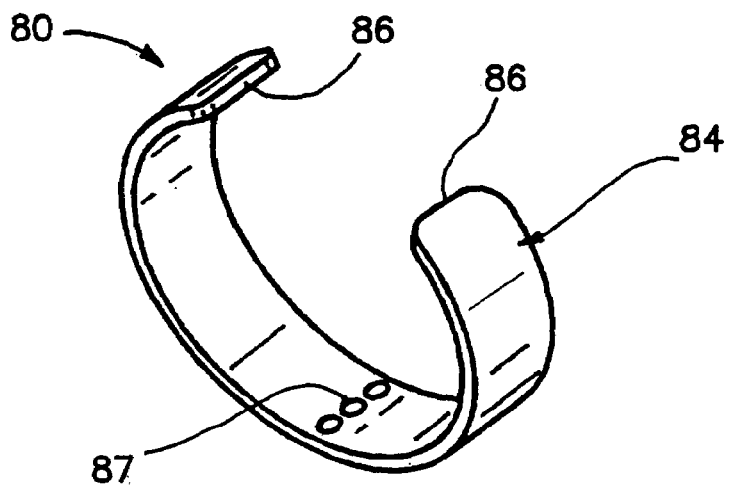
FIGS. 4a-4c show different views of another embodiment of an apparatus of the present invention.
Figure 4B:
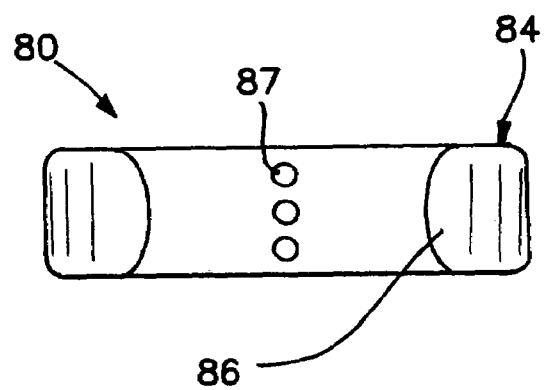
Figure 4C:
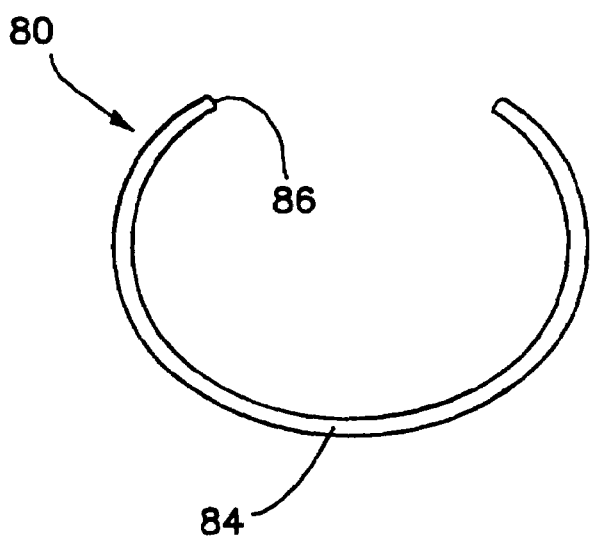

FIGS. 4a-4c show yet another apparatus 80 in accordance with the present invention, similar to the embodiment shown in FIGS. 2a-2e. This embodiment of the invention comprises an appliance 82 that is substantially cuff-shaped, having rounded or radiused, spaced apart end portions 86. The apparatus 80 is substantially solid, with the exception of apertures 87, and is preferably made entirely of a super-elastic material. Apertures 87 are provided for facilitating tissue ingrowth to prevent migration of the apparatus 80.

Preferably, in each of the embodiments of the apparatus of the invention, all edges of the appliance are rounded and are free of sharp portions, burrs and contaminants.

Preferably, each of the embodiments shown and described is comprised of highly elastic, biocompatible materials. More preferably, the apparatus of the present invention preferably comprises a super-elastic material, specifically, a nickel titanium (NiTi) alloy.

Intrinsically, the present appliances made of such metals such as Nitinol provide reinforcement and/or support to the vessel or other body region without altering, or at least without substantially altering, the body tissues and without or interfering with the physiological structure of the tissue itself. Advantageously, the use of such metallic materials provides enhanced control of the degree of stiffening and/or reinforcement of the vessel or other body region because the intrinsic properties of the appliance itself, for example the dimensions and resiliency thereof, are relied upon to treat the patient's condition. This is in contrast to treating a patient with a device intended to induce or promote one or more tissue reactions, for example, fibrosis, other scarring of tissues and the like reactions, near the device to effect stiffening or other changes in the body region.

For general background purposes, a description of the benefits of Nitinol for use in the present invention follows. Additional details of this alloy can be obtained from readily available sources and/or will be known to those of skill in the art.

Nickel titanium (also known as Nitinol) is in the class of materials known as shape memory alloys. A thermoelastic martensitic phase transformation in the material is responsible for its extraordinary properties. These properties include the shape memory effect, super-elasticity, and high damping capability.

Nitinol has the ability to absorb large amounts of strain energy and release it as the applied strain is removed. Nitinol also has excellent torqueability and kink resistance. Advantageously, super-elastic Nitinol alloys provide a constant force over a large strain range.

The present apparatus preferably comprise a Nitinol material, more preferably with a ratio of the two constituents, nickel and titanium, at about 50 atomic percent each (about 55 percent by weight of nickel).

The properties of Nitinol can be modified by changes in alloy composition, mechanical working, and heat treatment, as known to those of ordinary skill in the art. The specific alloy used for the apparatus of the present invention will be selected mainly for its super-elastic effect rather than its shape memory effect.

Super-elastic Nitinol alloys are preferably used in the apparatus of the present invention to take advantage of a stress-induced martensitic transformation in order to achieve extreme amounts of flexibility and kink resistance. It is known that an alloy of NiTi can behave super-elastically if its Active $A_f$ temperature is just below the use temperature. For example, alloys which are intended to be super-elastic at room temperature are generally produced with their Active $A_f$ temperatures just below room temperature in the range of 0 to 20 degrees C. A super-elastic material will not be super-elastic at all temperatures, but will exhibit good super-elastic properties in a temperature window extending from the Active $A_f$ temperature up to a temperature which is about 50 degrees C. above Active $A_f$. Therefore a material with an Active $A_f$ of about 15 degrees C. will exhibit good super-elasticity up to about 65 degrees C. which means that the material will exhibit good super-elasticity at both room temperature and body temperature (37 degrees C.).

Nitinol is also the preferred material for the apparatus of the present invention due to its excellent biocompatibility, very high corrosion resistance, and excellent cytocompatibility. In addition, the nickel in NiTi is chemically joined to the titanium in a strong intermetallic bond, so the risk of reaction, even in patients with nickel sensitivity, is extremely low. Additional details on nickel titanium alloys are known to those of ordinary skill in the art and are provided for example in Jervis, U.S. Pat. No. 6,306,141, which is incorporated herein in its entirety by this specific reference.

Figure 5:
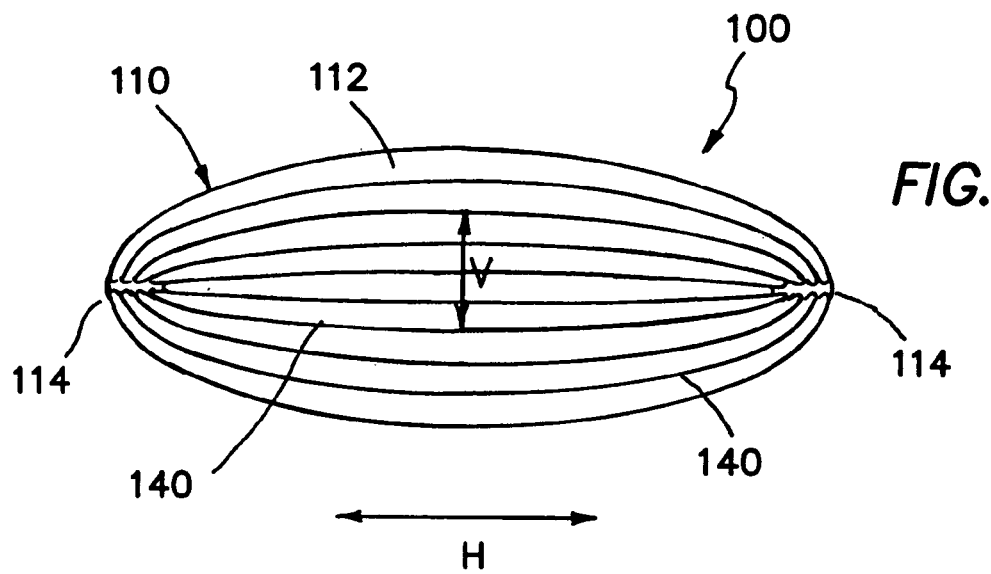
FIG. 5 shows a plan view of another embodiment of an apparatus of the present invention.

Another embodiment of the apparatus of the invention is shown in FIG. 5 and in several additional views in FIGS.

6a-6e. This embodiment of the invention generally comprises an apparatus 100 for maintaining patency, of a body region of the human or animal. The apparatus 100 generally comprises an appliance 110 having a non-circumferential configuration. More particularly, the appliance comprises a body portion 112 and end portions 114 spaced apart by the body portion 112. The appliance 110 may be in the form of a substantially circular or oblong, for example, rectangular, oval or elliptical configuration. The appliance is preferably structured to exert a sufficient force, more preferably a sufficient substantially constant radial force, on the body region, for example, walls of the region, to maintain or cause the vessel or other body region to be dilated or patent, so that it is substantially open or unobstructed.

Figure 6A:
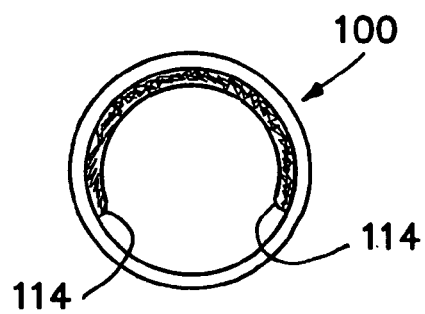
Figure 6B:
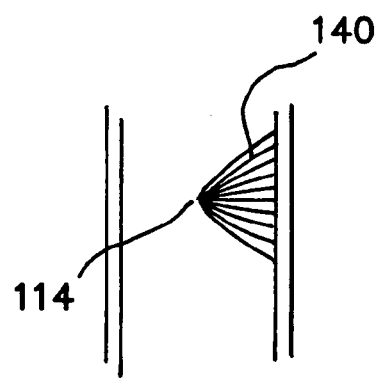
Figure 6C:
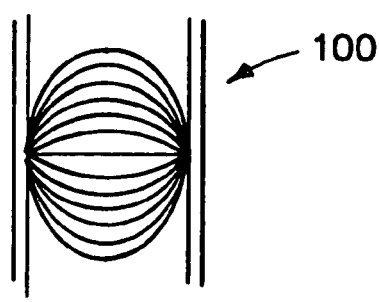

As shown in FIGS. 6a, 6f and 6g, the appliance 110 is structured to take on a deployed configuration when located within the vessel or other body region, such that the end portions 114 are spaced apart from each other by other than the body portion (for example, the end portions 114 are shown spaced apart by a portion of the vessel wall in FIG. 6a), the end portions 114 overlap each other (as shown in FIG. 6g) or the end portions 114 directly contact each other (as shown in FIG. 6f).

During a dynamic, wave-like or peristaltic motion of the vessel or other body region, the apparatus 100 may move, contract and expand to take on all three of these deployed configurations in varying degrees. The apparatus 100 is structured to be sufficiently resilient to allow for such dynamic motion with little or no loss in hoop strength over an extended period of wear.

The appliance is structured to form a relatively flat configuration when in other than the deployed configuration. For example, the apparatus 100 is shown in an undeployed, flat configuration in FIG. 6d. Alternatively, the appliance may be structured to form a pre-curved configuration, having a diameter of curvature larger than the diameter of curvature of the region, e.g. inner lumen, walls to be supported or opened. Advantageously, the apparatus 100 may be formed entirely from a unitary flat sheet of material that is laser cut into the desired configuration. Using a flat elastic or super-elastic sheet of material or a sheet pre-curved to a diameter larger than that of the target body region, for example, vessel, the appliance, once implanted into the body region, will apply continuous opening pressure to the vessel walls. Preferably, the corners are rounded to reduce the possibility of tissue trauma.

Advantageously, the appliance 110, when located in the body region has a resiliency and flexibility in multiple directions. For example, the appliance 110 can be arched (for example in a direction out of the page in FIG. 5), flexed or stretched along a horizontal plane (for example, in a direction indicated by double headed arrow H in FIG. 5), and contracted and expanded in a vertical direction (indicated by double headed arrow V in FIG. 5). Generally, the apparatus 100 is structured to dynamically conform to various degrees and directions of curvature of the body region.

For example, in the preferred embodiment shown in FIG. 5, the appliance 110 takes the form of a flat oval (FIG. 5 and FIG. 6d) when located outside the human or animal body region, and can be pre-curved for example, by heat-treatment, to form an open ended, concave configuration such as shown in FIGS. 6a-6c and 6e. For example, the appliance 110 may be in the form of an oval having a length of about 50 mm (formed to a semicircular curved diameter of about 30 mm) and a height of about 20 mm.

As shown most clearly in FIG. 5 the appliance 110 has a length defined between spaced apart, radiused end portions 114, and the appliance comprises a plurality of flexible wire or ribbon struts 140, which preferably extend between the radiused end portion extending along a substantial portion of the length of the appliance 110. The struts 140 may bow outwardly as shown to define the oval or elliptical configuration of the appliance 110 in its undeployed state. For example, the appliance 110 may comprise between about 0.2 and about 50 struts or more, and preferably between about 6 and about 20 struts, for example about 10 struts.

In the embodiment shown in FIG. 5, the appliance 110 includes ten (10) struts 140, each having a thickness of about 0.005" (or about 0.1 mm) and a width of about 0.010" (or about 0.2 mm). This design has been found to provide the required flexibility in at least three dimensions or directions of motion, and preferably, in addition, twisting motion, without exhibiting significant fatigue over an extended period of wear/time in service requiring dynamic movement, for example, in each of the above modes of motion.

The length, number, thickness, and width of the struts may be varied to produce a desired opening (hoop strength) pressure on the vessel or to reduce or increase the surface area of the struts which are in contact with the vessel.

The design of the apparatus 100 allows for variable hoop strength as measured along different points of the circumference of the appliance 110. In addition, the design allows improved vertical collapse/deformation of the vessel, for example, allowing peristalsis type movement of solids through the vessel.

Preferably, the appliance 110 is laser cut from a flat sheet of material, for example a flat sheet of Nitinol material. Advantageously, the appliance 100 has no loose, soldered, or woven edges and is substantially smooth on all surfaces thereof. Optionally, after being cut from the sheet of material, the appliance 110 may be heat-treated to take on a preformed curve. The appliance may be electropolished to ensure smooth edges and surfaces, for example, in order to reduce or completely eliminate the occurrence of fibrosis or a fibrotic response by the tissues of the vessel or other body region being treated.

FIGS. 5 and 6d show the appliance 110 at rest and outside the body. As shown, the appliance may be substantially flat and somewhat two-dimensional prior to implantation in the body. In other words, the appliance may be structured to form a relatively flat configuration when in other than the deployed configuration. When provided in a vessel or other body region of a patient for maintaining patency of the region, the appliance is curved for example, with a convex surface pressing against the tissues to be supported.

FIG. 6a shows one example of the appliance 110 in a vessel in cross-sectional view transverse to the vessel, the appliance forming a substantially semi-circular area of support to the vessel. In some embodiments however, and/or for other vessels or other body regions which the invention is used, the end portions 114 may contact one another (FIG. 6f) or may overlap (FIG. 6g).

The appliance 110 is preferably structured to be self expanding with a controlled length during such expansion. This can be achieved by suitable selection of super-elastic materials, preferably Nitinol, and appropriate selection of strut length and other dimensions. The appliance also is preferably structured to have a relatively atraumatic nature of all surfaces thereof and of the curved end portions. In addition, the appliance 110 is structured to exhibit the ability to be delivered in a minimal diameter access manner by rolling the appliance onto itself within a catheter or by folding the appliance 110 such that end portions 114 are temporarily secured together. Preferably, the appliance 110 is designed to be configurable as a flat sheet, or have a curve of a relatively larger diameter than the body region in order that the appliance 110 will exert constant force on the body region.

The appliance of 110 may be tailored to be effective in a variety of patients and in a variety of different body regions that would benefit from the consistent support provided by such an appliance. For example, the size and structure of the appliance can be selected to accommodate a specific need for example, to maintain patency or openness of an artery, vein, trachea, nasal cavity, esophagus, biliary tract, colon or other vessel or other body region. The amount of force provided by the appliance can be modified by appropriate selection of the number of struts, width and/or thickness of struts, and/or surface area covered by the struts, for example. Generally, as the struts become thinner and take up less surface area, the appliance will become more compliant and will move and flex with less radial force exerted thereby and will flex to a greater extent without permanent deformation.

In any event, the apparatus can be modified, within the scope of the invention, to provide an appropriate amount of force necessary to provide adequate support to maintain patency of the vessel or other body region while allowing for the dynamic motion of the region and normal healthy functioning of the region.

The struts 140 may be designed to compress and expand along with the walls inner lumen or tissues of the body region during the normal action of the body region. The super-elastic nature of the appliance 110 allows the appliance to recover from each flexion with no kinking or weakening of the original structure.

In some embodiments, although not shown, vertically disposed struts may also be provided. In other embodiments, the struts may be shaped as wave forms or s-shaped. In yet other embodiments, although not shown, cushioned end members may be provided on the end portions of the appliance 110 in order to enhance comfort and/or proper fit.

The apparatus 100 of the present invention can be deployed within a body region using conventional techniques, for example, conventional techniques currently utilized for deployment of conventional stents into a body region.

Alternatively, the following method may be used for deployment of an apparatus in accordance with the invention. The apparatus 100 shown in FIGS. 6a-6f is particularly well suited for deployment in a body region using the following method.

Accordingly, the present invention also provides a method for maintaining patency or causing to become patent, open or unobstructed, a body region, for example a collapsed or obstructed artery, vein, trachea, nasal cavity, esophagus, biliary tract, colon, or other vessel or body region of a human or an animal. The method in accordance with the invention generally comprises the steps of providing a flat or pre-curved member (for example, appliance 110), pulling end portions (for example end portions 114) of the flat or pre-curved member together to form a folded configuration (see FIG. 7) and holding or temporarily securing the end portions 114 together by means of a grasper, clamp, hemostat, suture (for example, a bioresorbable suture), and/or suitable means for temporarily holding the end portions together in contact with one another. The method further comprises the steps of placing the member in the folded or pinched configuration, into a body region, for example, and releasing the end portions, thereby allowing the member to reconfigure or expand radially within the body region. The reconfigured or expanded member preferably provides a substantially constant radial force against walls or other tissues of the body region.

The method may further comprise the step of repositioning the member while the member is located within the body region and/or the step of removing the member from the body region. This may be accomplished by folding the member into the pinched configuration shown in FIG. 7, and withdrawing the member from the body region.

FIG. 7 shows the apparatus 100 in a folded configuration, with graspers or hemostat pinching, or holding together, end portions 114, prior to the member being inserted into a body vessel.

As shown in FIG. 8a, an apparatus 310 of another embodiment of the present invention may be structured and adapted to be secured to the body region being treated by being surgically implanted into a wall 322 of the region, for example, directly beneath the region's mucosal layer, (hereinafter, "submucosally"), for example, by being pulled, with a surgical needle for example, or otherwise introduced into and beneath the mucosal layer such that the apparatus 310 at least partially circumscribes the region. Apparatus 310 may comprise and have a structure similar to any of the apparatus, for example appliance 30, 50, 50a, 60, 80, 100, described and shown elsewhere herein.

In another similar embodiment of the invention, shown in FIG. 8b, the apparatus 410 comprises one or more elements, or struts 412, spaced apart from one another and sized and structured to be submucosally implanted into a vessel 420 having a longitudinal axis. Even more specifically, the apparatus 410 may comprise one or more separate elongated struts 412 that are sized and structured to be implanted into walls 424 of such a vessel 420 in alignment with the longitudinal axis of the vessel 420 to provide support thereto.

FIG. 9 shows a simplified perspective view of another apparatus 1600 in accordance with the present invention. Apparatus 1600 comprises an appliance 1610 including an element 1612 having a transverse portion or component 1620 with spaced apart ends 1620a and 1620b, and two substantially longitudinal portions or members 1622a and 1622b depending from, and spaced apart by, the transverse portion 1620. Apparatus 1600 is a single, unitary structure made of metal, e.g. Nitinol and the like, or other material so as to inhibit or even substantially eliminate fibrosis or a fibrotic response or other reaction from the tissues of the body region when the apparatus is placed in the body region.

Preferably, each of the two longitudinal portions 1622a and 1622b depends from a corresponding spaced apart end 1620a and 1620b, respectively, of the transverse portion 1620, as shown in FIG. 9.

Advantageously, the transverse portion or component 1620 is sized and structured to be situated along a wall or other surface of a vessel or other body region, to provide a radial force, or an opening force to the region. The transverse portion 1620 may be secured to the wall of the region by any suitable means, including one of the many means described elsewhere herein with respect to other embodiments of the present invention.

In one aspect of the invention, the appliance 1610 is surgically implanted into a vessel being treated such that the transverse portion 1620 is at least partially submucosally implanted along the wall of the vessel, and the longitudinal portions 1622a and 1622b are implanted in substantial alignment with, for example, substantially parallel to, a longitudinal axis of the vessel, for example, within opposing lateral walls of the vessel. Preferably, the longitudinal portions or members 1622a and 1622b are substantially entirely submucosally implanted within the vessel walls.

FIG. 9A shows a simplified perspective view of another apparatus 1700 of the invention substantially similar to the apparatus 1600 shown in FIG. 9. Unless otherwise expressly specified, apparatus 1700 is substantially identical to apparatus 1600, with like elements indicated by like reference numerals. Apparatus 1700 is placed in the vessel or other region in substantially the same way that apparatus 1600 is so placed.

Apparatus 1700 comprises appliance 1710 having a sloping, for example but not limited to, a downwardly sloping, transverse portion 1720 and two longitudinal portions 1722a and 1722b depending therefrom. In other words, whereas appliance 1610 defines a substantially 90 degree angle between the transverse portion 1620 and the longitudinal portions 1622a and 1622b, the appliance 1710 defines an acute, or alternatively an obtuse (not shown), angle between the transverse portion 1720 and the longitudinal portions 1722a and 1722b.

In other related aspects of the invention, the appliance may have a transverse portion that defines a first angle with one of the longitudinal portions 1722a and 1722b and a second, different angle with the other one of the longitudinal portions 1722a and 1722b.

It is to be appreciated that the desired configuration of the apparatus 1600 or 1700, in many cases, will depend at least in part on the needs of the individual patient being treated.

The transverse portion 1720 of apparatus 1700 provides an additional component of longitudinal support as well as a radial opening force to the vessel or other body region. In alternate embodiments of apparatus 1700, the sloping transverse portion 1720 can be used with only one of the longitudinal portions 1722a and 1722b or without either or any of these longitudinal portions. In addition, apparatus including both transverse portions 1620 and 1720, with or without the longitudinal portions 1622a, 1622b, 1722a and/or 1722b, can be employed.

FIG. 10 shows another embodiment of the invention substantially similar to the embodiment shown in FIG. 9, wherein the apparatus 1800 comprises an appliance 1810 in a substantially planar, substantially, for example, radiused, squared U-shaped configuration. Like apparatus 1600, apparatus 1800 includes a transverse portion 1820 and longitudinal portions 1822a and 1822b depending therefrom. Unless otherwise expressly specified, apparatus 1800 is structured, is placed in the body region and functions substantially identically to apparatus 1600.

In apparatus 1800, transverse portion 1820 is substantially planar, that is, is not substantially bow shaped, when the appliance 1810 is at rest outside of the human or animal body.

Like appliance 1610, appliance 1810 is structured to be positioned within the body region, for example, at least partially submucosally implanted within a wall of the body region, for example, with transverse portion 1820 extending against a portion of the wall and longitudinal portions 1822a and 1822b extending substantially longitudinally with respect to a longitudinal axis of the vessel.

Transverse portion 1820 may have any suitable length, for example a length of about 20 mm and longitudinal portions 1822a and 1822b may each have a length in a range of about 3 cm to about 5 cm. Appliance 1810 may have a thickness, for example, a substantially uniform thickness, of about 1.0 mm. The dimensions set forth herein are illustrations and are not intended to limit the present invention. Any of such dimensions may vary widely, for example, by ± about 10%, or ± about 20%, or ± about 40%, or about ±60%, or more, so that the apparatus in accordance with the present invention may meet the treatment needs of a wide variety of individual patients.

FIG. 10A shows a magnified view of a radius of curvature of an outer edge of the angle between longitudinal portion 1822a and transverse portion 1820. The radius of curvature may be about 1.0 mm.

FIG. 10B shows a magnified view of a radius of curvature of a distal end of one of the longitudinal portions 1822a and 1822b. This radius of curvature may be about 0.5 mm.

FIG. 10C shows a side view of the apparatus of FIG. 10 in order to illustrate the relatively thin nature of the apparatus 1800, the apparatus 1800 having a thickness of about 0.2 mm.

When outside the body of the patient, for example, prior to implantation into a wall of a vessel, the apparatus at rest may have a substantially planar profile as shown in FIG. 10. This configuration is provided in order to simplify and facilitate implantation of the apparatus 1800. Once implanted, the apparatus 1800 conforms to the vessel wall while providing both radial and longitudinal support thereto.

Apparatus 1800 is substantially planar as shown in FIG. 30 after being cut from a planar sheet of material, for example, a metallic material, for example, Nitinol. In an alternative aspect of the invention, apparatus 1800 is heat treated prior to implantation, to take on a curved configuration, for example, similar to the curved configuration of apparatus 1700 shown in FIG. 29. The degree of curve may be selected based upon the needs of a particular patient. The heat treated curved apparatus 1800 may then be implanted into the vessel or other body region as described elsewhere herein.

FIG. 11 shows a plan view of another apparatus 1900 for maintaining or promoting patency of a vessel or other body region, in accordance with the present invention. The apparatus 1900 comprises an appliance 1910 including at least one substantially bow shaped element 1920. Apparatus 1900 is made of materials, e.g., metals, and to reduce or eliminate fibrosis, as discussed previously with regard to apparatus 1600, 1700 and 1800.

The bow shaped element 1920 is structured to be substantially entirely submucosally implanted within the region, for example along a weakened or collapsing wall of a vessel or other body region to provide an opening force to the region, such as described elsewhere herein.

Element 1920 includes a thickness and a length, wherein the thickness is smaller than the length as shown. Further, in some embodiments of the invention, element 1920 is sized and structured such that, when implanted into a wall of a vessel having a longitudinal axis, the element extends, longitudinally, a distance greater than the thickness of the element. For example, the element 1920 may be sized and structured to be implanted into a vessel wall in a relatively angular position with respect to the longitudinal axis of the vessel.

The at least one element 1920 may, in some embodiments of the invention, comprise a plurality of such elements 1920, meaning two or more such elements 1920, with each element having the same or different dimensions and structured and sized to be placed in a spaced apart, for example, laterally, and/or longitudinally spaced apart, relationship within the region. Alternatively, the two or more bow shaped elements 1920 may be structured and sized to be placed in the region in a crosswise arrangement, for example, in an arrangement such that the elements 1920 overlap or cross one another, or in any other suitable arrangement effective to maintain or promote patency of the region.

Depending upon where support is needed, and/or depending upon an amount or degree of support or reinforcement needed in a particular patient, and/or depending on one or more other factors, the element or elements 1920 may be disposed generally horizontal to the longitudinal axis of the vessel being treated or, alternatively, at any other suitable angle thereto.

Referring to both FIGS. 11 and 11A, element 1920 may substantially define an arc having a radius of curvature of about 63 mm. Each end of the element 1920 may have a radius of curvature about 0.5 mm. Element 1920 may have a length L, measured in a straight line between ends of the element 1920, of about 50 mm and an arched width W of about 5.0 mm, as shown. The element 1920 may have a width, for example, a substantially uniform width along the arc of the element 1920, of about 1.0 mm. The element 1920 may have a thickness of about 0.2 mm.

FIG. 12 shows a plan view of another apparatus 2000 comprising an apparatus 2010 including an element 2020 that, like element 1920, is substantially arcuate or bow shaped. This embodiment of the invention is substantially identical to the embodiment, apparatus 1900, shown in FIG. 11 and FIG. 11A, with the exception of some of the dimensions thereof.

Referring to both FIGS. 12 and 12A, element 2020 may substantially define an arc having a radius of curvature of about 35 mm. Each end of the element 2020 may have a radius of curvature about 0.5 mm. Element 2020 may have a length L, measured in a straight line between ends of the element 2020, of about 50 mm, an arched width W of about 10 mm. The element 2020 may have a width, for example, a substantially uniform width along the arc of the element 2020, of about 1.0 mm. The element 2020 may have a thickness of about 0.2 mm.

While this invention has been described with respect to various specific examples and embodiments, it is to be understood that the invention is not limited thereto and that it can be variously practiced within the scope of the following claims.

What is claimed is:

1. An apparatus for maintaining patency of a pharyngeal region of a human or animal body, the apparatus comprising:
    an appliance comprising a body portion and end portions spaced apart by the body portion, the body portion and the end portions together define an interior open space,
    the appliance being structured and sized to take on a deployed configuration when located within the pharyngeal region, such that (a) the interior open space remains open, (b) the end portions are spaced apart from each other by other than the body portion, the end portions overlap each other, or the end portions directly contact each other, and (c) the appliance exerts a force on the pharyngeal region to maintain the region substantially open or unobstructed, or to cause the region to be maintained substantially open or unobstructed.

2. The apparatus of claim 1 wherein the appliance is structured to form a relatively flat configuration.

3. The apparatus of claim 1 wherein the appliance is configured and structured to be submucosally implanted into the pharyngeal region and defines a substantially flat configuration when in other than the deployed configuration.

4. The apparatus of claim 1 wherein the appliance comprises a super-elastic material.

5. The apparatus of claim 1 wherein the appliance comprises Nitinol.

6. The apparatus of claim 1 wherein the end portions are radiused.

7. The apparatus of claim 1 wherein the appliance has a length defined between the end portions, and the appliance comprises a plurality of struts extending along a substantial portion of the length.

8. The apparatus of claim 7 wherein said plurality of struts comprise a super-elastic material.

9. The apparatus of claim 7 wherein said plurality of struts comprise Nitinol.

10. The apparatus of claim 1 wherein the appliance comprises at least about 2 struts structured to be spaced apart from one another when implanted in the pharyngeal region.

11. The apparatus of claim 10 wherein the struts are sized and structured to be submucosally implanted in a vessel.

12. The apparatus of claim 11 wherein struts are sized and structured to be implanted in the vessel such that the struts are aligned along a longitudinal axis defined by the vessel.

13. A method for maintaining patency of or for causing to become patent, open or unobstructed, a pharyngeal region of a human or an animal, the method comprising the steps of:
    providing a flat or pre-curved member having a body portion and end portions spaced apart by the body portion, the body portion and the end portions together defining an interior open space;
    pulling end portions of the flat or pre-curved member together to form a folded configuration;
    holding or temporarily securing the end portions together;
    placing the member, in the folded configuration, into a pharyngeal region to be treated; and
    releasing the end portions from being held or secured together, thereby allowing the member to expand within the pharyngeal region so that the interior open space remains open.

14. The method of claim 13 wherein the expanded member within the pharyngeal region is effective to provide a substantially constant radial force against the walls or tissues of the pharyngeal region.

15. A method for maintaining patency of or for causing to become patent, open or unobstructed, a pharyngeal region of a human or animal, the method comprising the steps of:
    providing an elongated member having a desired stiffness and resiliency, the elongated member comprising a body portion and end portions spaced apart by the body portion, the body portion and the end portions together defining an interior open space; and
    implanting the elongated member submucosally into walls of the pharyngeal region in alignment with a longitudinal axis so that the interior open space remains open.

16. The method of claim 15 further comprising the step of providing another said elongated member;
    implanting the another said elongated member submucosally into the pharyngeal region in alignment with and spaced apart from the elongated member to provide support to the pharyngeal region.

17. The apparatus of claim 1 wherein the body portion and end portions are made of mesh construction.

18. The method of claim 13 wherein the body portion and the end portions are made of mesh construction.

19. The method of claim 15 wherein the body portion and the end portions are made of mesh construction.

20. The apparatus of claim 1, further comprising a needle for pulling the appliance into the mucosal layer of the vessel or other body region.

21. The apparatus of claim 15, wherein implanting the elongated member comprises pulling the elongate member into the mucosal layer with a needle.

22. A method for maintaining patency of or for causing to become patent, open or unobstructed, a pharyngeal region of a human or animal, the method comprising the steps of:

provide an elongated member having a desired stiffness and resiliency, the elongated member comprising a body portion and end portions spaced apart from the body portion, the body portion and the end portions together defining an interior open space;

introducing the elongated member into the pharyngeal region; and pulling the elongated member into the mucosal layer with a needle to at least partially implant the elongated member submucosally into walls of the pharyngeal region.

23. The method of claim 22, wherein the elongated member is implanted substantially entirely submucosally into the walls of the pharyngeal region.

24. The method of claim 22, wherein introducing the elongated member comprises:

pulling end portions of the elongated member together to form a folded configuration;

placing the elongated member into the vessel in the folded configuration; and releasing the elongated member within the vessel.

* * * * *